US009255280B2

(12) United States Patent
Hillyer

(10) Patent No.: US 9,255,280 B2
(45) Date of Patent: Feb. 9, 2016

(54) REMOVAL OF FERMENTATION INHIBITING COMPOUNDS FROM CITRUS WASTE USING SOLVENT EXTRACTION AND PRODUCTION OF ETHANOL FROM CITRUS WASTE

(75) Inventor: Gregory Loyde Hillyer, North Bethesda, MD (US)

(73) Assignee: JJ FLORIDA PROPERTIES LLC, Miami, FL (US)

( * ) Notice: Subject to any disclaimer, the term of this patent is extended or adjusted under 35 U.S.C. 154(b) by 1008 days.

(21) Appl. No.: 12/467,565

(22) Filed: May 18, 2009

(65) Prior Publication Data

US 2009/0291481 A1    Nov. 26, 2009

Related U.S. Application Data

(60) Provisional application No. 61/054,651, filed on May 20, 2008, provisional application No. 61/139,138, filed on Dec. 19, 2008.

(51) Int. Cl.
*C12P 7/06* (2006.01)
*C12P 19/02* (2006.01)
*C12P 19/14* (2006.01)

(52) U.S. Cl.
CPC . *C12P 7/06* (2013.01); *C12P 19/02* (2013.01); *C12P 19/14* (2013.01); *Y02E 50/17* (2013.01)

(58) Field of Classification Search
CPC .......... C12P 5/007; C12P 19/02; C12P 19/14; C12P 7/06; C12P 17/181; C12P 19/44; C12P 7/04; C12N 15/8243; Y02E 50/17; Y02E 50/343; C07C 11/21; C12Y 101/01088; C12Y 202/01007; C12Y 205/0101; C12Y 402/03047
See application file for complete search history.

(56) References Cited

U.S. PATENT DOCUMENTS

| | | | |
|---|---|---|---|
| 1,781,788 A | 11/1930 | Matzka | |
| 2,276,420 A | 3/1942 | Rosenfeld | |
| 2,561,072 A | 7/1951 | Reich | |
| 2,686,146 A | 8/1954 | Buswell et al. | |
| 2,984,601 A | 5/1961 | Sudarsky et al. | |
| 3,112,248 A | 11/1963 | Sudarsky et al. | |
| 3,845,218 A | 10/1974 | Mussell | |
| 3,966,984 A | 6/1976 | Cocke et al. | |
| 4,113,573 A | 9/1978 | Gerow | |
| 4,291,124 A | 9/1981 | Muller et al. | |
| 4,316,956 A | 2/1982 | Lützen | |
| 4,403,034 A | 9/1983 | Rogers et al. | |
| 4,425,433 A | 1/1984 | Neves | |
| 4,488,912 A | 12/1984 | Milch et al. | |
| 4,503,079 A | 3/1985 | King et al. | |
| 4,547,226 A | 10/1985 | Milch et al. | |
| 4,564,595 A | 1/1986 | Neves | |
| 4,612,286 A | 9/1986 | Sherman et al. | |
| 4,637,835 A | 1/1987 | Nagle | |
| 4,650,689 A | 3/1987 | Hedrick | |
| 4,818,250 A | 4/1989 | Whitworth | |
| 4,915,707 A | 4/1990 | Whitworth | |
| 4,952,504 A | 8/1990 | Pavilon | |
| 5,061,497 A | 10/1991 | Thacker et al. | |
| 5,079,011 A | 1/1992 | Lommi et al. | |
| 5,135,861 A | 8/1992 | Pavilon | |
| 5,177,008 A | 1/1993 | Kampen | |
| 5,177,009 A | 1/1993 | Kampen | |
| 5,186,722 A | 2/1993 | Cantrell et al. | |
| 5,220,105 A | 6/1993 | Kruger, Jr. et al. | |
| 5,252,107 A | 10/1993 | Wilkins, Jr. | |
| 5,348,871 A | 9/1994 | Scott et al. | |
| 5,354,851 A | 10/1994 | Graves | |
| 5,403,612 A | 4/1995 | Huang | |
| 5,501,713 A | 3/1996 | Wilkins, Jr. | |
| 5,522,995 A * | 6/1996 | Cockrem | 210/637 |
| 5,554,520 A | 9/1996 | Fowler et al. | |
| 5,607,486 A | 3/1997 | Wilkins, Jr. | |
| 5,710,030 A | 1/1998 | Anderson | |
| 5,846,787 A | 12/1998 | Ladisch et al. | |
| 6,251,643 B1 | 6/2001 | Hansen et al. | |
| RE37,629 E | 4/2002 | Wilkins, Jr. | |
| 6,509,180 B1 | 1/2003 | Verser et al. | |
| 6,569,653 B1 | 5/2003 | Alard et al. | |
| 6,703,227 B2 | 3/2004 | Jakel et al. | |
| 6,740,508 B2 | 5/2004 | Ulrich et al. | |
| 6,962,722 B2 | 11/2005 | Dawley et al. | |
| 7,083,954 B2 | 8/2006 | Jakel et al. | |
| 7,101,691 B2 | 9/2006 | Kinley et al. | |
| 7,102,057 B2 | 9/2006 | Lanahan et al. | |
| 7,115,298 B2 | 10/2006 | Keithly et al. | |
| 7,138,257 B2 | 11/2006 | Galli et al. | |
| 2002/0160469 A1 | 10/2002 | Ingram et al. | |
| 2003/0077771 A1 | 4/2003 | Verser et al. | |
| 2003/0194788 A1 | 10/2003 | Jakel et al. | |
| 2003/0224496 A1 | 12/2003 | Jakel et al. | |
| 2004/0091983 A1 | 5/2004 | Veit et al. | |
| 2004/0170731 A1 | 9/2004 | Subramaniam et al. | |
| 2004/0253696 A1 | 12/2004 | Grichko | |
| 2005/0054064 A1 | 3/2005 | Talluri et al. | |
| 2005/0118692 A1 | 6/2005 | Kinley et al. | |
| 2005/0239181 A1 | 10/2005 | Lewis et al. | |
| 2006/0035354 A1 | 2/2006 | Galli et al. | |

(Continued)

OTHER PUBLICATIONS

Roy, et al, Supercritical Carbon Dioxide Extraction of the Volatiles from the Peel of Japanese Citrus Fruits, Journal of Essential Oil Research, Jan./Feb. 2007, pp. 78-83.
Abbas, Charles A., Lignocellulosics to ethanol: meeting ethanol demand in the future, The Alcohol Textbook $4^{th}$ Edition, 2003, pp. 41-57, Ch. 5, K.A. Jacques (ed.), T.P. Lyons (ed.), D.R. Kelsall (ed.).
Ben-Shalom, Noach, Hinderance of Hemicellulose and Cellulose Hydrolysis by Pectic Substances, Journal of Food Science, 1986, pp. 720-721; 730, vol. 51, No. 3.

(Continued)

*Primary Examiner* — Debbie K Ware
(74) *Attorney, Agent, or Firm* — Feldman Gale, P.A.

(57) ABSTRACT

The present invention relates to novel processes for producing ethanol from citrus waste using suitable solvent extractions to reduce the presence of fermentation inhibiting compounds, such as limonene, from citrus waste. The extraction can be performed before or after the polysaccharides present in aqueous mixtures comprising citrus waste are converted into fermentable sugars.

17 Claims, No Drawings

(56) References Cited

U.S. PATENT DOCUMENTS

| | | |
|---|---|---|
| 2006/0121589 A1 | 6/2006 | Dunn-Coleman et al. |
| 2006/0127999 A1 | 6/2006 | Verser et al. |
| 2006/0154353 A1 | 7/2006 | Duan et al. |
| 2006/0177916 A1 | 8/2006 | Stewart et al. |
| 2006/0260011 A1 | 11/2006 | Carter et al. |
| 2006/0275882 A1 | 12/2006 | Martinez-Gutierrez et al. |
| 2006/0281157 A1 | 12/2006 | Chotani et al. |
| 2006/0292677 A1 | 12/2006 | Ostrander |
| 2007/0031953 A1 | 2/2007 | Dunson, Jr. et al. |
| 2007/0037267 A1 | 2/2007 | Lewis et al. |
| 2007/0082385 A1 | 4/2007 | Smith et al. |
| 2007/0099278 A1 | 5/2007 | Aare |
| 2007/0134780 A1 | 6/2007 | Grichko |
| 2007/0134781 A1 | 6/2007 | Agblevor |
| 2007/0141688 A1 | 6/2007 | Henderson et al. |
| 2007/0141689 A1 | 6/2007 | Bhargava et al. |
| 2007/0141691 A1 | 6/2007 | Hirl |
| 2007/0155001 A1 | 7/2007 | Veit et al. |
| 2007/0178567 A1 | 8/2007 | Lewis |
| 2007/0178569 A1 | 8/2007 | Leschine et al. |
| 2007/0184541 A1 | 8/2007 | Karl et al. |

OTHER PUBLICATIONS

Bothast, R.J., et al., Biotechnological process for conversion of corn into ethanol, Appl Microbiol Biotechnol, 2005, pp. 19-25, vol. 67.

Cameron, Randall, et al., Mapping Demethylated Block Size and Distribution in Pectin from Citrus Processing Waste, Research Project: Enhanced Utilization of Carbohydrates and Polysaccharides from Citrus Processing Waste Streams, USDA Agricultural Research Service, Oct. 21, 2004, Florida.

Cellulose Conversion Key to Fuel of the Future, National Renewable Energy Laboratory, Aug. 1994.

Doran, Joy Bethune, et al., Fermentations of Pectin-Rich Biomass with Recombinant Bacteria to Produce Fuel Ethanol, Applied Biochemistry and Biotechnology, 2000, pp. 141-152, vol. 84-86.

Echeverria, Ed, et al., Effect of Cell Wall Hydrolysis on Brix in Citrus Fruit, Proc. Fla. Stat Hort. Soc., 1988, pp. 150-154, vol. 101.

Flores, Alfredo, Citrus Peel Waste a Potential Source of Ethanol, USDA Agricultural Research Service, Apr. 6, 2006.

Golias, Helen, et al., Characteristics of cellulose preparations affecting the simultaneous saccharification and fermentation of cellulose to ethanol, Biotechnology Letters, 2000, pp. 617-621, No. 22.

Grohmann, K., et al., Fermentation of Galacturonic Acid and Other Sugars in Orange Peel Hydrolysates by the Ethanologenic Strain of *Escherichia coli*, Biotechnology Letters, Mar. 1994, pp. 281-286, vol. 16, No. 3.

Grohmann, K., et al., Fermentation of Sugars in Orange Peel Hydrolysates to Ethanol by Recombinant *Escherichia coli* KO11, Applied Biochemistry and Biotechnology, 1995, pp. 423-435, vol. 51/52.

Grohmann, K., et al., Fractionation and Pretreatment of Orange Peel by Dilute Acid Hydrolysis, Biosource Technology 54, 1995, pp. 129-141, Florida.

Grohmann, K., et al., Hydrolysis of Orange Peel With Pectinase and Cellulase Enzymes, Biotechnology Letters, Dec. 1992, pp. 1169-1174, vol. 14, No. 12.

Grohmann, K., et al., Production of Ethanol from Enzymatically Hydrolyzed Orange Peel by the Yeast Saccharomyces cerevisiae, Applied Biochemistry and Biotechnology, 1994, pp. 315-327, vol. 45/46.

How Do We Get d-Limonene and Orange Oil?, What is d-Limonene, http://www.floridachemical.com/whatisd-limonene.htm, retrieved May 15, 2007, p. 2.

Ingledew, W.M., Continuous fermentation in the fuel alcohol industry: How does the technology affect yeast?, The Alcohol Textbook 4$^{th}$ th Edition, 2003, pp. 135-143, Ch. 11, K.A. Jacques (ed.), T.P. Lyons (ed.), D.R. Kelsall (ed.)

Jacobs, P.B. & H.P. Newton, http://www.journeytoforever.org/bifuel_library/ethanol_motherearth/meCh3.html, U.S. Dept. Agr., Miscl. Publ 327, Dec. 1938, retrieved May 15, 2007.

Kelsall, Dave R., et al., Grain dry milling and cooking procedures: extracting sugars in preparation for fermentation, The Alcohol Textbook 4$^{th}$ Edition, 2003, pp. 9-21, Ch. 2, K.A. Jacques (ed.), T.P. Lyons (ed.), D.R. Kelsall (ed.).

Kelsall, Dave R., et al., Practical management of yeast: conversion of sugars to ethanol, The Alcohol Textbook 4$^{th}$ Edition, 2003, pp. 121-133, Ch. 10, K.A. Jacques (ed.), T.P. Lyons (ed.), D.R. Kelsall (ed.).

Kesterson, J.W., et al., By-Products and Specialty Products of Florida Citrus, Agricultural Experiment Stations, Institute of Food, University of Florida, Gainesville, Bulletin 784, Dec. 1976, pp. 1-119.

Kling, S.H., et al., Enhancement of Enzymatic Hydrolysis of Sugar Cane Bagasse by Steam Explosion Pretreatment, Biotechnology and Bioengineering, 1987, pp. 1035-1039, vol. XXIX.

Larson, Jim, et al., Managing the Four Ts of cleaning and sanitizing: time, temperature, titration and turbulence, The Alcohol Textbook 4$^{th}$ Edition, 2003, pp. 299-318, Ch. 21, K.A. Jacques (ed.), T.P. Lyons (ed.), D.R. Kelsall (ed.).

Luzio, Gary A., Determination of Galacturonic Acid Content of Pectin Using a Microtiter Plate Assay, Proc. Fla. State Hort. Soc., 2004, pp. 416-421, vol. 117, Florida.

Madson, P.W., Ethanol distillation: the fundamentals, The Alcohol Textbook 4$^{th}$ Edition, 2003, pp. 319-336, Ch. 22, K.A. Jacques (ed.), T.P. Lyons (ed.), D.R. Kelsall (ed.).

Marshall, M.R., et al., A Comparison of Enzymatic and Lime Treatments for Extraction of Alcohol Soluble Solids from Citrus Peel, Journal of Food Science, 1985, pp. 1211-1212, vol. 50.

McAloon, Andrew, et al., Determining the Cost of Producing Ethanol from Corn Starch and Lignocellulosic Feedstocks, National Renewable Energy Laboratory, pp. 1-30, Appendix, Oct. 2000.

Meredith, John, Understanding energy use and energy users in contemporary ethanol plants, The Alcohol Textbook 4$^{th}$ Edition, 2003, pp. 355-361, Ch. 25, K.A. Jacques (ed.), T.P. Lyons (ed.), D.R. Kelsall (ed.).

Narendranath, N. V., Bacterial contamination and control in ethanol production, The Alcohol Textbook 4$^{th}$ Edition, 2003, pp. 287-298, Ch. 20, K.A. Jacques (ed.), T.P. Lyons (ed.), D.R. Kelsall (ed.).

Nishio, Naomichi, et al., Production of Macerating Enzymes of Mandarin Orange Peel by Fungal Cultures, European J. Appl. Microbiol. Biotechnology, 1979, pp. 371-378, vol. 6.

Open Hopper Chopper Pump, http://industrialpaints.globelspec.com/FeaturedProducts/Detail/Seepex/Open_Hopper_Chopper_Pump/17 Retrieved May 15, 2007.

Philippidis, George P., et al., Study of the Enzymatic Hydrolysis of Cellulose for Production of Fuel Ethanol by the Simultaneous Saccharification and Fermentation Process, Biotechnology and Bioengineering, 1993, pp. 846-853, vol. 41.

Power, Ronan F., Enzymatic conversion of starch to fermentable sugars, The Alcohol Textbook 4$^{th}$ Edition, 2003, pp. 23-32, Ch. 3, K.A. Jacques (ed.), T.P. Lyons (ed.), D.R. Kelsall (ed.).

Research Project: Enhanced Utilization of Carbohydrates and Polysaccharides from Citrus Processing Waste Streams, USDA Agricultural Research Service, Retrieved May 15, 2007, Florida.

Russell, Inge, Understanding yeast fundamentals, The Alcohol Textbook 4$^{th}$ Edition, 2003, pp. 85-117, Ch. 9, K.A. Jacques (ed.), T.P. Lyons (ed.), D.R. Kelsall (ed.).

Wilkins, Mark, Citrus Peel Ethanol. Florida's Biofuel for the Future, Research Project: Enhanced Utilization of Carbohydrates and Polysaccharides from Citrus Processing Waste Streams, USDA Agricultural Research Service, Oct. 21, 2004, Florida.

Wilkins, Mark R., et al., Effect of Seasonal Variation on Enzymatic Hydrolysis of Valencia Orange Peel Waste, Proc. Fla. State Hort. Soc., 2005, pp. 419-422, vol. 118, Florida.

Wilkins, Mark R., et al., Hydrolysis of grapefruit peel waste and cellulose and pectinase enzymes, Bioresource Technology (2006), doi:10 1016/j.biotech 2006.06.022.

Zhou, Weiyang, et al., Economic analysis of ethanol production from citrus peel waste, Research Project: Enhanced Utilization of Carbohydrates and Polysaccharides from Citrus Processing Waste Streams, USDA Agricultural Research Service, May 10, 2007, Florida.

\* cited by examiner

REMOVAL OF FERMENTATION INHIBITING COMPOUNDS FROM CITRUS WASTE USING SOLVENT EXTRACTION AND PRODUCTION OF ETHANOL FROM CITRUS WASTE

CROSS REFERENCE TO RELATED APPLICATIONS

This application claims priority to U.S. Provisional Application Ser. No. 61/054,651, filed May 20, 2008, and U.S. Provisional Application Ser. No. 61/139,138, filed Dec. 19, 2008, the entire disclosures of which are hereby incorporated herein by reference in their entireties.

FIELD OF THE INVENTION

The present invention provides processes for producing ethanol from citrus waste wherein the level of fermentation-inhibiting compounds found in citrus waste is reduced using a pre-fermentation extraction step to lower the level of fermentation-inhibiting compounds in the fermentation feedstock.

BACKGROUND OF THE INVENTION

Florida produces approximately 5 million tons of orange peel waste each year. Most of this peel waste is dried, pelletized, and sold as beef or milk cattle feed filler commonly referred to as citrus pulp pellets.

High gasoline prices, overdependence on foreign oil, and a continuing demand for renewable energy sources have led to increased research interest in the general field of citrus peel waste conversion, and in particular, to the transformation of peel waste to ethanol. Current processes generally involve hydrolyzing citrus peel comprising a complex mixture of polysaccharides to provide fermentable sugars, fermenting the sugars to produce ethanol, and isolating the ethanol and other by-products.

Unfortunately, some compounds found in citrus peel or produced during the steps converting citrus peel into fermentable sugars act as fermentation inhibitors in the conversion of these sugars to ethanol. Among these compounds, limonene, a terpene-based component in citrus peel, is known to impede fermentation processes (See Grohmann, et al., *Production of Ethanol from Enzymatically Hydrolyzed Orange Peel by the Yeast Saccharomyces Cerevisiae*, Applied Biochemistry and Biotechnology, Vol. 45 (1994)). Limonene is generally understood to provide a natural defense for citrus against bacteria, viruses, molds, and other organisms and to inhibit fermentation by typical processes that would yield ethanol. It has been estimated that, for efficient fermentation, limonene in the citrus peel waste should be below 3000 parts per million and perhaps even below 1500 ppm.

Stewart et al. (U.S. Patent Application No. 2006/0177916) describes a process of producing ethanol from citrus waste where limonene is removed prior to fermentation. The disclosed process includes limonene removal via evaporation and steam stripping from citrus peel, hydrolysis of the limonene-stripped citrus peel waste, and fermentation of the resulting hydrolysis mixture to produce ethanol (or simultaneous hydrolysis and fermentation). The steam-stripped limonene may be recovered by condensation. Stewart does not address the possibility of employing extraction as a means of reducing the level of fermentation-inhibiting compounds found in citrus waste or the complex polysaccharide or sugars derived therefrom.

Among the problems associated with steam-stripping and similar processes is the substantial usage of energy (e.g., electricity, fuel consumption, etc.) that is necessary to carry out the processes. Such energy expenditures and particularly problematic where the overall goal is to produce alternative fuel sources, such as fossil fuel replacements, because ideally the energy input will be minimized to yield an overall energy-efficient process. Although Stewart discloses the use of centrifuging as an alternative method for removing limonene, Stewart does not address any issues associated with energy usage or otherwise suggest extraction as a means for reducing the level of fermentation-inhibiting compounds.

Previous attempts to use extraction to remove fermentation-inhibiting compounds prior to fermentation have proved unsuccessful. For example, Grohmann (Grohmann, et al., *Production of Ethanol from Enzymatically Hydrolyzed Orange Peel by the Yeast Saccharomyces Cerevisiae*, Applied Biochemistry and Biotechnology, Vol. 45, 1994) attempted to remove limonene from an aqueous citrus waste mixture using solvent extraction but abandoned the approach because of the formation of inseparable emulsions with a series of organic solvents. Ultimately, Grohmann used filtration to remove the limonene based on the inability to successfully carry out the extraction. Such solutions do not address the problems presented by the extraction and would be problematic on scale-up.

Although extraction has recently been used under certain conditions to remove volatiles from the peel of citrus fruits (Bhupesh, et al., *Supercritical Carbon Dioxide Extraction of the Volatiles from the Peel of Japanese Citrus Fruits*, J. Essent. Oil Res., 19, 78-84 (2007)), the disclosed procedures did not involve a pre-fermentation extraction step designed to lower the level of fermentation-inhibiting compounds in a feedstock for the production of ethanol. Furthermore, Bhupesh does not teach or suggest converting one or more polysaccharides contained in the citrus waste into fermentable sugars either before or after the extraction, or in turn, fermenting these sugars into ethanol in the absence of the fermentation-inhibiting compounds.

Inasmuch as there is a continuing demand for alternative and/or renewable energy resources, a need to reduce dependence on foreign oil supplies, and a need to reduce or stabilize gasoline prices for example, there is still an unfulfilled need for a specific and effective solution to address one or more of these issues. In view of the above, it is highly desirable to find new methods of eliminating limonene, other similar terpene components, or other fermentation-inhibiting compounds from citrus waste in order to enhance the production of ethanol therefrom. The present invention is directed to these, as well as other important ends.

SUMMARY OF THE INVENTION

Generally, it is an object of the present invention to provide methods for removing or isolating from a citrus waste mixture, limonene, similar terpene compounds, or other compounds capable of inhibiting fermentation of the sugars derived from citrus waste.

It is another object of the invention to provide methods for producing ethanol from citrus waste, which includes removing or isolating limonene, similar terpene components, or other compounds found in citrus waste that are capable of inhibiting fermentation of the fermentable sugars derived from citrus waste.

It is another object of the invention to provide methods for producing ethanol from citrus waste, comprising providing an aqueous mixture comprising citrus waste, extracting with a suitable solvent or solvent mixture at least a portion of one or more fermentation-inhibitory compounds contained in the citrus waste, converting one or more polysaccharides contained in the citrus waste into fermentable sugars, and fermenting the sugars to produce ethanol.

In certain embodiments, the present invention provides methods for producing ethanol from citrus waste, comprising:
- a. contacting citrus waste with supercritical $CO_2$ to provide a citrus waste with a reduced level of at least one compound capable of inhibiting a fermentation of sugars derived from citrus waste;
- b. adding water to the citrus waste from step (a);
- c. hydrolyzing the aqueous mixture of citrus waste from step (b) to provide a aqueous mixture comprising fermentable sugars derived from the citrus waste (saccharification);
- d. fermenting the aqueous mixture obtained from step (c) to produce an aqueous mixture containing ethanol; and,
- e. removing the ethanol from the mixture from step (d).

In certain embodiments, the present invention provides methods for producing ethanol from citrus waste, comprising:
- a. hydrolyzing an aqueous mixture of citrus waste to provide a aqueous mixture comprising fermentable sugars derived from the citrus waste (saccharification);
- b. optionally removing water from the hydrolyzed citrus waste from step (a);
- c. contacting the citrus waste from step (a) or step (b) with supercritical $CO_2$ to provide a citrus waste with a reduced level of at least one compound capable of inhibiting a fermentation of sugars derived from citrus waste;
- d. optionally adding water to the citrus waste from step (c);
- e. fermenting the aqueous mixture obtained from step (c) or step (d) to produce an aqueous mixture containing ethanol; and,
- f. removing the ethanol from the mixture from step (e).

In certain embodiments, the present invention provides novel methods for producing ethanol from citrus waste, comprising:
- a. contacting citrus waste with supercritical $CO_2$ to provide a citrus waste with a reduced level of at least one compound capable of inhibiting a fermentation of sugars derived from citrus waste;
- b. adding water to the citrus waste from step (a);
- c. hydrolyzing the aqueous mixture of citrus waste from step (b) to provide a aqueous mixture comprising fermentable sugars derived from the citrus waste (saccharification);
- d. fermenting the aqueous mixture obtained from step (c) to produce an aqueous mixture containing ethanol; and,
- e. removing the ethanol from the mixture from step (d).

In certain embodiments, the present invention provides novel methods for producing ethanol from citrus waste, comprising:
- (a) extracting a mixture comprising citrus waste containing one or more fermentation-inhibitory compounds with an extraction solvent to provide an extracted citrus waste mixture having a reduced concentration of at least one of the fermentation-inhibitory compounds; and
- (b) producing ethanol from the extracted mixture.

In certain embodiments, the present invention provides novel methods for producing ethanol from citrus waste, comprising:
- (a) providing a mixture which comprises citrus waste, wherein the concentration of at least one fermentation-inhibitory compound in the citrus waste has been reduced by solvent extraction; and
- (b) producing ethanol from the aqueous mixture.

In certain embodiments, the present invention provides novel methods for producing ethanol from citrus waste, comprising:
- (a) providing a mixture which comprises citrus waste having a reduced concentration of at least one fermentation-inhibitory compound; and
- (b) producing ethanol from the aqueous mixture.

It is another object of the invention to provide methods for producing ethanol from citrus waste, comprising:
- a. contacting an aqueous citrus waste mixture with a suitable extraction solvent (or solvent mixture) to provide an aqueous citrus waste mixture with a reduced level of at least one compound capable of inhibiting a fermentation of sugars derived from citrus waste;
- b. fermenting the aqueous citrus waste mixture with a reduced level of at least one compound capable of inhibiting a fermentation of sugars derived from citrus waste obtained from step (a) to produce a mixture containing ethanol; and,
- c. isolating the ethanol from the fermented mixture from step (b).

It is another object of the invention to provide methods for producing ethanol from citrus waste, comprising:
- a. contacting an aqueous citrus waste mixture with a suitable extraction solvent (or solvent mixture) to provide an aqueous citrus waste mixture with a reduced level of at least one compound capable of inhibiting a fermentation of sugars derived from citrus waste;
- b. hydrolyzing the aqueous citrus waste mixture with a reduced level of at least one compound capable of inhibiting a fermentation of sugars derived from citrus waste from step (a) to provide a mixture comprising fermentable sugars derived from citrus waste (saccharification);
- c. fermenting the mixture comprising fermentable sugars derived from citrus waste obtained from step (b) to produce a mixture containing ethanol; and,
- d. isolating the ethanol from the fermented mixture from step (c).

It is another object of the invention to provide methods for simultaneous saccharification and fermentation.

It is another object of the invention to provide methods for producing ethanol from citrus waste, comprising:
- a. hydrolyzing an aqueous citrus waste mixture to provide an aqueous citrus waste mixture comprising fermentable sugars derived from citrus waste (saccharification);
- b. contacting the aqueous citrus waste mixture comprising fermentable sugars derived from citrus waste from step (a) with a suitable extraction solvent (or solvent mixture) to provide an aqueous citrus waste mixture with a reduced level of at least one compound capable of inhibiting a fermentation of sugars derived from citrus waste;
- c. fermenting the aqueous citrus waste mixture with a reduced level of at least one compound capable of inhibiting a fermentation of sugars derived from citrus waste obtained from step (b) to produce a mixture containing ethanol; and
- d. isolating the ethanol from the fermented mixture from step (c).

It is another object of the invention to provide methods for recovering limonene, similar terpene compounds, or other compounds capable of inhibiting fermentation from a suitable extraction or solvent mixture.

It is another object of the invention to provide methods for producing ethanol from citrus waste, which includes a step wherein fermentation-inhibiting compounds, such as limonene, present in citrus waste are substantially removed by extraction with a suitable solvent or a mixture of suitable solvents.

These and other objects, which will become apparent during the following detailed description, have been achieved by the inventors' discovery that certain fermentation-inhibiting compounds typically found within fermentable sugar process streams or their citrus waste precursors may be removed from the citrus waste via extraction with suitable extraction solvents, including supercritical fluid solvents.

DETAILED DESCRIPTION OF THE PREFERRED EMBODIMENTS

While not wishing to be bound by theory, it is believed that the unsaturated bonds in limonene, similar terpene components, or other compounds capable of inhibiting fermentation are, at least in part, responsible for inhibiting ethanol fermentation processes such as those described herein. The present invention is in part based on the expectation that removal of limonene, similar terpene components, or other compounds capable of inhibiting fermentation will produce a citrus waste composition that may be more readily fermented, either simultaneously with or after hydrolysis of the citrus peel polysaccharides.

It is also believed, in theory, that the complexity of citrus waste mixtures, and in particular, the physical and electronic properties of the compounds present therein, are responsible for the formation of the emulsions during liquid solvent extraction that have rendered the process challenging or unsuccessful. For example, the carbohydrates (pectin, cellulose, etc.) and other oligomers found in citrus peel waste contain hydrophobic and hydrophilic moieties which may dramatically affect their behavior in various solvents. By contrast, limonene is an aliphatic, hydrophobic compound that is unlikely to share affinity with water soluble solvents. Other constituents, such as wax, lipids and acids further increase the complexity of the mixture. Further complexity results following the initial milling and jet cooking of the peel to expose the constituents and prepare them for chemical manipulation. Accordingly, the use of certain organic solvents, such as alcoholic solvents, may create an environment wherein a biphasic mixture is unobtainable. Under such circumstances, the separation of certain organic components, such as limonene, may not be readily achieved or achieved at all.

The present invention is based, in part, on the discovery of suitable extraction solvents that reduce or minimize the adverse impact of certain compounds found in citrus waste mixtures, such as emulsion-forming compounds, on the extraction of the citrus waste to remove other compounds capable of inhibiting a fermentation of sugars derived from the citrus waste, and preferably, substantially avoid such effect, permitting a more efficient isolation of organic compounds from citrus waste.

As employed above and throughout the disclosure, the following terms, unless otherwise indicated, shall be understood to have the following meanings.

As used herein, the term "suitable extraction solvent" refers to a relatively non-polar, organic solvent or mixture thereof that is immiscible with water and capable of dissolving organic constituents, preferably limonene, other terpene components, or derivatives thereof. Suitable extraction solvents should function in the extraction process so as to avoid the formation of substantial emulsions that do not permit the aqueous/solvent layers to be separated. In some instances, the solvating properties of the suitable extraction solvent are present under typical extraction conditions of about atmospheric pressure and/or about room temperature.

By way of example and without limitation, suitable extraction solvents employed under typical extraction conditions include dichloroethane, chloroform, chlorobutane, hydrocarbons, and ether and aryl (or aromatic) solvents or any mixtures thereof.

Other suitable extraction solvents, such as supercritical fluid extraction solvents, have suitable solvating properties at particular conditions of temperature and/or pressure known to one of skill in the art. By way of example and without limitation, suitable common supercritical fluid extraction solvents and their critical properties include those listed in the following table:

| Fluid | Critical Temperature (K) | Critical Pressure (bar) |
|---|---|---|
| Carbon dioxide | 304.1 | 73.8 |
| Ethane | 305.4 | 48.8 |
| Ethylene | 282.4 | 50.4 |
| Propane | 369.8 | 42.5 |
| Propylene | 364.9 | 46.0 |
| Trifluoromethane (Fluoroform) | 299.3 | 48.6 |
| Chlorotrifluoromethane | 302.0 | 38.7 |
| Trichlorofluoromethane | 471.2 | 44.1 |
| Cyclohexane | 553.5 | 40.7 |
| n-Pentane | 469.7 | 33.7 |
| Toluene | 591.8 | 41.0 |

As used herein, the term "hydrocarbon solvent" includes without limitation, any linear or branched $C_5$-$C_{12}$alkane- or unsubstituted or lower alkyl branched $C_5$-$C_{12}$cycloalkane-based solvent or mixture thereof. Non-limiting examples include pentane, hexane, heptane, octane, nonane, decane, dimethyloctane, trimethylpentane, cyclohexane, cycloheptane, decalin, methylcyclohexane, or any mixture thereof. In certain preferred embodiments, the hydrocarbon solvent is heptane, octane, nonane, decane, dimethyloctane, trimethylpentane, cyclohexane, cycloheptane, decalin, methylcyclohexane, any of the isomeric menthanes, or any mixture thereof, more preferably octane, nonane, decane, dimethyloctane, trimethylpentane, cyclohexane, cycloheptane, decalin, methylcyclohexane, or any mixture thereof.

As used herein, the term "ether solvent" includes without limitation, any hydrocarbon solvent or mixture thereof, wherein hydrocarbon solvent is as defined above and, wherein at least one non-terminus carbon atom in the alkane or cycloalkane chain has been replaced by an oxygen atom. For example, ether solvents include diethyl ether, diethoxymethane, ethylene glycol dimethyl ether, ethylene glycol diethyl ether, diethylene glycol dimethyl ether, diethylene glycol diethyl ether, triethylene glycol dimethyl ether and t-butyl methyl ether. Cyclic ether solvents include, for example, tetrahydrofuran, tetrahydropyran, and 1,4-dioxane, and the like.

As used herein, the term "aryl solvent" or "aromatic solvent" includes without limitation, any aromatic ring containing solvent or mixture thereof, for example, benzene, toluene, ethylbenzene, o-xylene, m-xylene or p-xylene, mestiylene, or durene, or mixture thereof.

As used herein, the term "citrus" or "citrus fruit" includes all citrus fruits commercially available, preferably those in substantial commercial production, with orange and grapefruit being even more preferred.

As used herein, the term "citrus peel waste," "CPW," "citrus waste" or "citrus waste solids" comprises the peel, segment membranes (pulp), seeds and/or other components of citrus fruit.

As used herein, the term "converting one or more polysaccharides contained in the citrus waste" refers to any process whereby polysaccharides are broken down, or hydrolysed, at least in part, to fermentable sugar moieties. In certain aspects, the converting is carried out by organisms, such as for example, in a secondary fermentation step. In other aspects, the hydrolysis is carried out by the addition of enzymes (saccharification). Any method known to the skilled artisan for the hydrolysis of polysaccharides into fermentable sugars is contemplated to be within the ambit of the invention.

As used herein, the term "substantially saccharify" refers to a saccharification process wherein more than about 50%, preferably more than about 60%, more preferably than about 75%, still more preferably more than about 90%, yet more preferably more than about 95% of the saccharide bonds present in polysaccharides that are capable of saccharification to fermentable sugars have been hydrolyzed. For example, after citrus waste is substantially saccharified, more than about 50% of the fermentable sugars bound within the polysaccharide component of citrus waste are available as fermentable sugars.

As used herein, the terms "compound capable of inhibiting the fermentation" and "fermentation-inhibitory compounds" each refer to any compound present in citrus waste and/or its hydrolyzates whose presence during fermentation of sugars derived from citrus waste for the production of ethanol adversely affects the fermentation.

As used herein, the terms "reducing the level of a compound capable of inhibiting the fermentation" and "reducing the level of one or more fermentation-inhibitory compounds" each refer to any operation that decreases the level of the inhibiting compound in any fermentation feedstock but does not require removal of the inhibiting compound to provide the reduced level. Preferred reduced levels include about 90% or less, preferably about 75% or less, more preferably about 50% or less, still more preferably about 25% or less, yet more preferably about 10% or less of the level of the at least one compound capable of inhibiting the fermentation originally present in the fermentation feedstock, with about 5% or less being even more preferred.

As used herein, the term "fermentation feedstock" refers to any aqueous citrus waste mixture or further modified mixture thereof. Examples include citrus waste, hydrolyzed citrus waste, hydrogenated citrus waste, extracted citrus waste and the like, and any combinations thereof.

In certain embodiments, the present invention is directed to novel methods for producing ethanol from citrus waste.

In certain embodiments, the present invention is directed to removing or isolating from a citrus waste mixture, limonene, similar terpene compounds, or other compounds capable of inhibiting fermentation of the sugars derived from citrus waste.

In certain embodiments, the present invention is directed to novel methods for producing ethanol from citrus waste, which includes removing or isolating limonene, similar terpene components, or other compounds found in citrus waste that are capable of inhibiting fermentation of the fermentable sugars derived from citrus waste.

In certain embodiments, removal of the fermentation-inhibiting compounds is carried out after the polysaccharides have been hydrolyzed. In other embodiments, removal of the limonene, similar terpene components, or other compounds capable of inhibiting fermentation is carried out prior to hydrolyzing the polysaccharides, for example, on solid, preferably particulate, citrus peel waste or an aqueous mixture thereof. In these and other embodiments, the modified citrus peel waste mixture may then be hydrolyzed and fermented.

In certain embodiments, the present invention is directed to novel methods of producing ethanol from citrus waste, which includes a step wherein fermentation-inhibiting compounds, such as limonene, present in citrus waste or fermentable sugars derived therefrom, are substantially removed by extraction with a suitable solvent or a mixture of suitable solvents.

Accordingly, in certain embodiments, the present invention provides methods for producing ethanol from citrus waste, comprising: providing an aqueous mixture comprising citrus waste, extracting with a suitable solvent or solvent mixture at least a portion of one or more fermentation-inhibitory compounds contained in the citrus waste, converting one or more polysaccharides contained in the citrus waste into fermentable sugars, and fermenting the sugars to produce ethanol.

In certain embodiments, the present invention provides methods for producing ethanol from citrus waste, comprising:
a. extracting the aqueous mixture comprising citrus waste to remove at least a portion of one or more fermentation-inhibitory compounds from the aqueous mixture;
b. converting at least a portion of the one or more polysaccharides contained in the aqueous mixture from step (a) into fermentable sugars; and
c. fermenting the aqueous mixture from step (b) to produce a fermented mixture containing ethanol.

In certain embodiments, the present invention provides methods for producing ethanol from citrus waste, comprising:
a. converting into fermentable sugars one or more citrus waste polysaccharides contained in the aqueous mixture comprising citrus waste;
b. extracting the aqueous mixture from step (a) to remove at least a portion of one or more fermentation-inhibitory compounds; and
c. fermenting the extracted aqueous mixture from step (b) to produce a fermented mixture containing ethanol.

In certain embodiments, the present invention provides methods for producing ethanol from citrus waste, comprising:
a. contacting an aqueous citrus waste mixture with a suitable extraction solvent (or solvent mixture) to provide an aqueous citrus waste mixture with a reduced level of at least one compound capable of inhibiting a fermentation of sugars derived from citrus waste;
b. fermenting the aqueous citrus waste mixture with a reduced level of at least one compound capable of inhibiting a fermentation of sugars derived from citrus waste obtained from step (a) to produce a mixture containing ethanol; and,
c. isolating the ethanol from the fermented mixture from step (b).

In certain embodiments, the present invention provides methods for producing ethanol from citrus waste, comprising:
a. contacting an aqueous citrus waste mixture with a suitable extraction solvent (or solvent mixture) to provide an aqueous citrus waste mixture with a reduced level of at least one compound capable of inhibiting a fermentation of sugars derived from citrus waste;
b. hydrolyzing the aqueous citrus waste mixture with a reduced level of at least one compound capable of inhibiting a fermentation of sugars derived from citrus waste from step (a) to provide a mixture comprising fermentable sugars derived from citrus waste (saccharification);

c. fermenting the mixture comprising fermentable sugars derived from citrus waste obtained from step (b) to produce a mixture containing ethanol; and, d. isolating the ethanol from the fermented mixture from step (c).

In certain embodiments, the saccharification and fermentation of steps (b) and (c) noted immediately above are carried out simultaneously.

In certain embodiments, the present invention provides methods for producing ethanol from citrus waste, comprising:

a. hydrolyzing an aqueous citrus waste mixture to provide an aqueous citrus waste mixture comprising fermentable sugars derived from citrus waste (saccharification);

b. contacting the aqueous citrus waste mixture comprising fermentable sugars derived from citrus waste from step (a) with a suitable extraction solvent (or solvent mixture) to provide an aqueous citrus waste mixture with a reduced level of at least one compound capable of inhibiting a fermentation of sugars derived from citrus waste;

c. fermenting the aqueous citrus waste mixture with a reduced level of at least one compound capable of inhibiting a fermentation of sugars derived from citrus waste obtained from step (b) to produce a mixture containing ethanol; and d. isolating the ethanol from the fermented mixture from step (c).

In certain embodiments of the invention, the suitable extraction solvents are those solvents employed under typical extraction conditions. Alternatively, preferred as suitable extraction solvents are those more commonly referred to as supercritical fluid extraction solvents.

Extraction efficiency with suitable extraction solvents to some extent depends on the particle size of the oil-containing material (e.g., the citrus peels and seeds). As such, it may be beneficial to reduce (e.g., shred, grind, press, mill, or squeeze) the particle size of the citrus waste in order to create more surface area for the extraction. Particle size reduction may also benefit the saccharification process as well as allow for easier transport of the waste (e.g., pumping). Thus, in other embodiments, the citrus waste, prior to hydrolyzing, may be mechanically reduced in size to form particles with and average particle size of less than about 1, 0.9, 0.8, 0.7, 0.6, 0.5, 0.4, 0.3, 0.2, and/or 0.1 inches. Alternatively, the citrus waste may be even further reduced to form particles with an average particle size of less than about 0.09, 0.08, 0.07, 0.06, 0.05, 0.04, 0.03, 0.02, and/or 0.01 inches. These particle sizes can be achieved using a variety of methods, including the methods of grinding and/or milling, and such machines as hammer mills and/or grinding pumps. The particle sizes described herein represent average particle sizes and are not meant to be limiting. By way of example, in a mixture of ground citrus peel with average diameter of about 0.5 inches, some of the particles will be about 0.5 inches, while others may be greater or less, such that the average diameter of particles is about 0.5 inches.

The milled citrus waste is preferably added to a vessel suitable for performing the extraction. The size, shape and features of the vessel may be dictated by the circumstances which will be apparent to one of skill in the art. In certain situations, it may be advantageous to have a valve at the bottom of the vessel so that the aqueous and organic layers may be easily removed. The extraction solvent is charged into the vessel, but the order of addition of the citrus waste and extraction solvent is not critical and may simply be a matter of convenience. Furthermore, additional water and/or brine may be optionally added at various stages to provide the appropriate extraction layer depth (or phase depth), volume or separation. In certain situations, the citrus waste may be extracted without any addition of water or dilution. Preferably, however, the citrus waste is taken up in water to form an aqueous layer that may be contacted with the extraction solvent.

Preferred extraction solvents are those that do not demonstrate significant hydrogen bonding. In this regard, hydrocarbon solvents are particularly suitable, including alkane- or cycloalkane-based solvents or mixtures thereof. Of the hydrocarbon solvents, alkane solvents are more preferred. Pentane, hexane, and heptane are even more preferred. Hexane is still more preferred. Alternatively preferred are cycloalkane solvents, more preferably substituted cyclohexane solvents, still more preferably alkyl substituted cyclohexane solvents. Of the substituted cycloalkane solvents, the various menthane (isopropyl-methylcyclohexane) isomers or mixtures thereof (1,2-, 1,3-, and/or 1,4-isopropyl-methylcyclohexane), the 1,3- and 1,4-menthanes and/or mixtures thereof are preferred, more preferably the 1,4-isomer, also known as para-menthane. As recognized in the art, any of these isomers may be cis or trans isomers, or mixtures thereof. All of these isomers and mixtures thereof are contemplated to be within the ambit of the invention. Ether solvents may also serve as suitable extraction solvents. A preferred ether solvent is diethyl ether. Aryl solvents also serve as suitable extraction solvents. More preferred aryl solvents are toluene, o-xylene, m-xylene and p-xylene, mesitylene and durene or mixtures thereof. It will be appreciated that, depending upon the application, mixtures of any of the extraction solvents may be possible and preferred.

Once the materials are charged to the vessel, the hydrolyzed or un-hydrolyzed citrus waste is extracted with the extraction solvent. Typically, the aqueous citrus waste will be contacted with the extraction solvent accompanied by some type of agitation (e.g., stirring or shaking, etc.) for a time sufficient to extract the limonene, similar terpene components, or other compounds found in citrus waste that are capable of inhibiting fermentation. Preferably, the level is below about 3000 ppm in the citrus waste. It may be necessary to add additional solvent, water or brine to effectuate adequate separation of the layers. It may also be desirable to remove one or more layers from the vessel, re-charge the citrus waste, and repeat the extraction with fresh extraction solvent until a suitable level of limonene is achieved.

In certain embodiments, use of a suitable extraction solvent reduces the presence of limonene, similar terpene components, or other compounds capable of inhibiting fermentation to well below 3000 parts per million based on the weight of citrus waste in the pre-fermentation mixture. For example, additional lower levels of the fermentation inhibiting compounds include below about 2500, preferably below about 2000, more preferably below about 1500, with below about 1000 ppm based on the weight of citrus waste in the pre-fermentation mixture being even more preferred. It should be noted that complete removal of fermentation-inhibiting compounds is expected to be difficult and likely unnecessary. Therefore, some (e.g., about 10 to about 500 ppm) fermentation inhibiting compounds may remain after extraction.

The suitable extraction solvent (now containing limonene and/or other organic constituents) is subsequently separated and preferably transferred to a separate tank. The extraction solvent may be separated from the citrus waste by any of a range of techniques known to the skilled artisan, including for example, use of a decanter or by employing a valve in the bottom of the reaction vessel. If desired, the extraction solvent may be removed, for example, by distillation or evaporation, to isolate the limonene, similar terpene component(s) or other fermentation-inhibiting compound(s). If desired, the solvent can be captured and recycled. Depending upon the composition, fractional distillation may be employed. Other traditional techniques, such as back-washing of the extraction solvent with water (or brine), the use of a drying agent, etc., may be employed.

In certain embodiments, the presence of water may diminish the efficiency of the extraction. Thus, it may be advantageous to perform the extraction on the citrus waste in the absence of water, or less water than typically required for a post-extraction efficient conversion of the polysaccharides to fermentable sugars. Using such a procedure, an amount of water may then be added after extraction to the citrus waste to form a citrus waste slurry for the saccharification and/or fermentation of the citrus waste or fermentable sugars therefrom. Optionally, the citrus waste can be partially dehydrated prior to extraction, especially when supercritical fluid extractions are employed, as discussed below. For example, the level of water can be reduced to about 25, 20, 15, 10, or 5%/wt based on the weight of citrus waste in the mixture.

As noted, the solvent extraction may be carried out through the use of suitable supercritical fluids. For example, if the temperature and pressure are both increased from STP to at least about the critical point, supercritical fluids may adopt properties midway between a gas and a liquid and are therefore have solvating properties. Within these parameters, the actual operating conditions chosen for extraction with the supercritical fluids will depend, among other things, on the size of the system as will be appreciated by the skilled artisan. For example, by varying the temperature (e.g., 31.2, 40, 60, 80, to 100° C. or more) and pressure (e.g., 75, 80, 85, 90, 95, 100, 125, to about 150 bar or more) of carbon dioxide above its critical temperature and critical pressure, not only provides carbon dioxide as a supercritical fluid, but may modify certain of its properties to fine tune the desired solvating properties in a particular supercritical extraction. While any combined temperature and pressure above the critical point may provide a suitable supercritical extraction solvent, more typically, carbon dioxide extractions are operated at between about 32 and about 49 degrees centigrade and at a pressure of between about 73 and about 250 bar. Likewise, other suitable extraction solvents may achieve supercriticality at or above their critical temperature and pressure, and/or any variations of temperature and/or pressure above these threshold limits.

In preferred embodiments where supercritical solvents are employed as suitable extraction solvents, any solvent capable of attaining supercriticality may be used. Selection of the appropriate supercritical solvent may be made, for example, based on the desired temperature and pressure parameters to be employed, the substrate to be extracted and its form, and the like. Such solvents include for example, carbon dioxide, ethane, ethylene, propane, propylene, trifluoromethane, chlorotrifluoromethane, trichlorfluoromethane, cyclohexane, n-pentane, toluene, more preferably carbon dioxide.

To perform the supercritical solvent extraction, the milled citrus waste may be transferred to a downward flow vertical extractor. Supercritical fluid from a compressor unit may be introduced into the extractor, which is maintained at a temperature and pressure appropriate for the extraction and will depend upon the particular solvent employed. The citrus waste is extracted with supercritical fluid for a time sufficient to extract the limonene, preferably to a level below about 3000 ppm. The limonene (or other fermentation-inhibiting compound) containing supercritical fluid may be delivered to a separator tank (e.g., after passing through a reducing valve), and the limonene or other fermentation-inhibiting compound(s) recovered by separation from the supercritical fluid as it moves out of its supercritical phase and loses is solvating properties. The resulting gaseous supercritical fluid may then be exhausted to the atmosphere or recycled to the extractor.

Examples of extractors that can be used for the supercritical fluid extraction include a vertical extractor with downward or upward solvent flow and/or a horizontal extractor. The temperature and pressure used in the extractor may be varied to maintain the supercritical nature of the supercritical fluid and also to enhance extraction. The precise temperature and pressure chosen will depend on a number of variables including the type and size of extractor, the amount of material being extracted, the size of the citrus waste particles, the moisture content of the particles, and the desired flow rate of the extraction.

Although citrus waste contains certain fermentable sugars, the complex polysaccharides (carbohydrates) are preferably broken down to provide more (e.g., glucose, fructose, sucrose, etc.). This can be accomplished by hydrolysis (saccharification) of the polysaccharides. In certain embodiments, hydrolyzing the citrus peel waste is performed by contacting the citrus waste with at least one enzyme capable of complex carbohydrate (polysaccharide) hydrolysis. A number of enzymes and enzyme classes are known to be have this activity, including pectinases, hemicellulases, cellulases, and beta-glucosidases. Mixtures of one or more of these enzymes, other enzymes, and/or enzyme classes are also within the ambit of the invention.

In yet other embodiments, the fermenting is performed by contacting the saccharified (i.e., hydrolyzed) mixture with an ethanol producing organism selected from a yeast, bacteria, or fungi. Examples of suitable organisms include brewer's yeast, *S. cerevisiae*, and *E. coli* strain KO11. The pH and temperature of the mixture can be adjusted to best suit the selected organism. As noted above, in another embodiment, the fermentation can be performed simultaneously with the saccharification (a process known as simultaneous saccharification and fermentation ("SSF")).

In certain other embodiments, the ethanol formed by fermentation is isolated from the fermentation beer, preferably by distillation. This distillation can be run continuously by removing a portion of the fermentation mixture (e.g., the beer), distilling, and then returning the remaining portion to the fermentation reaction. The distillation can also be performed on the entire fermentation reaction mixture, for example once the level of ethanol has begun to degrade the fermentation reaction. If other constituents are present in the fermentation mixture, they too may be removed by distillation. In certain embodiments, fractional distillation may be employed to not only remove any volatile compounds from the beer, but preferably further resolve at least some of the components contained within the volatile mixture that may be removed by distillation from the beer.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

When ranges are used herein for physical properties of compounds, or reaction conditions, such as the wt./wt. ratios of suitable extraction solvent(s) to citrus waste, temperatures and/or reaction pressures, all combinations and subcombinations of ranges and specific embodiments therein are intended to be included.

Other features of the invention will become apparent in the course of the following descriptions of exemplary embodiments that are given for illustration of the invention and are not to be construed as limiting the appended claims. Employing the methodologies herein described or cited, ethanol may be readily provided from citrus waste. The invention is further described in the following prophetic examples.

EXAMPLES

Example 1

Simultaneous Saccharification and Fermentation (SSF)

Raw citrus waste is ground to achieve a particle size of less than one half inch using a hammer mill. The ground waste is optionally diluted with water and transferred to a reaction vessel suitable for performing a solvent extraction. The extraction solvent hexane is introduced into the extractor. Optionally, additional water and/or brine is added at various stages to provide the appropriate layer depth, volume or separation. The citrus waste is extracted (contacted with the extraction solvent with agitation) for a time sufficient to extract the limonene to a level below about 3000 ppm in the citrus waste. The extraction solvent is separated and transferred to a separate tank where limonene and other organic constituents are recovered, for example, through distillation or evaporation. Optionally, the extraction solvent is recovered and recycled. Water is added to the remaining citrus waste to form a slurry, which is then subject to simultaneous saccarification and fermentation. This may be accomplished by transferring the citrus waste to a fermentation mixing tank. The pH of the slurry is measured and adjusted if necessary before addition of saccharification enzymes and any necessary adjustments with typical pH-adjusting compounds are made. Saccharification enzymes are added, followed by ethanol-producing $E.\ coli$ KO11. The contents of the tank are mixed until the desired level of ethanol is achieved. The beer is filtered into a distillation tank. Ethanol is distilled from the liquid. The solids from the fermentation tank (the stillage) are optionally pressed and dried.

Example 2

Procedure for Alternative Extraction and Fermentation

Aqueous raw citrus waste slurry is ground to achieve a particle size of less than one half inch using a hammer mill and transferred to a vessel suitable for performing a solvent extraction. The pH of the mixture is measured and adjusted if necessary with typical pH adjusting compounds before addition of saccharification enzymes. The saccharification enzymes are added and the tank is mixed to allow for hydrolysis. The hydrolyzed slurry is then transferred via a progressing cavity pump to vessel suitable for solvent extraction. The extraction solvent is introduced into the vessel. The citrus waste mixture is extracted with the extraction solvent for a time sufficient to extract the limonene to a level below about 3000 ppm. The extraction solvent is separated and transferred to a separate tank where limonene (and/or other organic constituent(s)) is recovered through distillation or evaporation. Optionally, the extraction solvent is recovered and recycled. Water is added to the remaining citrus waste to form a slurry which is then subject to fermentation. This may be accomplished by transferring the citrus waste to a fermentation mixing tank. The pH of the mixture is measured and adjusted if necessary before addition of the fermentation yeasts. $E.\ coli$ KO11 is added. The contents of the tank are mixed until a sufficient level of ethanol is achieved. The beer is filtered into a distillation tank. Ethanol is distilled from the liquid. The solids from fermentation tank are optionally dried and pressed.

Example 3

Simultaneous Saccharification and Fermentation (SSF)

Raw citrus waste is ground to achieve a particle size of less than one half inch using a hammer mill. The ground waste is transferred to a downward flow $CO_2$ vertical extractor. Supercritical $CO_2$ from a compressor unit is introduced into the extractor, which is maintained at about 8000 psi and 50° C. The citrus waste is extracted with supercritical $CO_2$ for a time sufficient to extract the limonene to a level below about 3000 ppm. The supercritical $CO_2$ containing limonene is passed through a heated reducing valve to a separator tank where extracted limonene is recovered. The extracted waste is then returned to ambient temperature and pressure. Water is added to the citrus waste to form a slurry, which is then transferred a fermentation mixing tank. The pH of the slurry is measured to determine if adjustment is necessary before addition of saccharification enzymes, and adjustment with typical pH adjusting compounds is made, if necessary. Saccharification enzymes are added, followed by ethanol-producing $E.\ coli$ KO11. The contents of the tank are mixed until a sufficient level of ethanol is achieved. The beer is filtered into a distillation tank. Ethanol is distilled from the liquid. The solids from the fermentation tank are dried for cattle feed.

Example 4

Procedure for Alternative Extraction and Fermentation

Aqueous raw citrus waste slurry is ground to achieve a particle size of less than one half inch using a hammer mill and transferred to a fermentation tank. The pH of the mixture is measured to determine if adjustment is necessary before addition of saccharification enzymes, and adjustment with typical pH adjusting compounds is made, if necessary. The saccharification enzymes are added, and the tank is mixed to allow for hydrolysis. The hydrolyzed slurry is then transferred via a progressing cavity pump to a downward flow $CO_2$ vertical extractor. Supercritical $CO_2$ from a compressor unit is introduced into the extractor, which is maintained at about 8000 psi and 50° C. The citrus waste mixture is extracted with supercritical $CO_2$ for a time sufficient to extract the limonene to a level below about 3000 ppm. The supercritical $CO_2$ containing limonene is passed through a heated reducing valve to a separator tank where extracted limonene is recovered. The extracted waste is then returned to ambient temperature and pressure and transferred to a fermentation mixing tank. The pH of the mixture is measured and adjusted if necessary before addition of the fermentation yeasts. $E.\ coli$ KO11 is added. The contents of the tank are mixed until a sufficient level of ethanol is achieved. The beer is filtered into a distillation tank. Ethanol is distilled from the liquid. The solids from fermentation tank are dried for cattle feed.

Numerous modifications and variations of the present invention are possible in light of the above teachings. It is therefore to be understood that within the scope of the appended claims, the invention may be practiced otherwise that as specifically described herein.

Each reference cited herein is hereby incorporated by reference in its entirety.

Embodiment 1

A method for producing ethanol from citrus waste, comprising:
  a. contacting an aqueous citrus waste mixture with a suitable extraction solvent (or solvent mixture) to provide an aqueous citrus waste mixture with a reduced level of at least one compound capable of inhibiting a fermentation of sugars derived from citrus waste;
  b. fermenting the aqueous citrus waste mixture with a reduced level of at least one compound capable of inhibiting a fermentation of sugars derived from citrus waste obtained from step (a) to produce a mixture containing ethanol; and,
  c. isolating the ethanol from the fermented mixture from step (b).

Embodiment 2

A method for producing ethanol from citrus waste of embodiment 1, comprising:
  a. contacting an aqueous citrus waste mixture with a suitable extraction solvent (or solvent mixture) to provide an aqueous citrus waste mixture with a reduced level of at least one compound capable of inhibiting a fermentation of sugars derived from citrus waste;
  b. hydrolyzing the aqueous citrus waste mixture with a reduced level of at least one compound capable of inhibiting a fermentation of sugars derived from citrus waste from step (a) to provide a mixture comprising fermentable sugars derived from citrus waste (saccharification);
  c. fermenting the mixture comprising fermentable sugars derived from citrus waste obtained from step (b) to produce a mixture containing ethanol; and,
  d. isolating the ethanol from the fermented mixture from step (c).

Embodiment 3

A method of embodiment 1 or 2, further comprising providing the citrus waste to step (a) in the form of particles with an average particle size of less than about 0.5 inches.

Embodiment 4

A method of embodiment 1, 2, or 3, wherein the average particle size of the citrus waste is less than about 0.1 inches.

Embodiment 5

A method of embodiment 1, 2, 3, or 4, wherein the providing comprises milling or grinding the citrus waste.

Embodiment 6

A method of embodiment 1, 2, 3, 4, or 5, wherein the the citrus waste is contacted with at least one enzyme capable of complex carbohydrate hydrolysis to substantially saccharify the polysaccharides contained in the citrus waste.

Embodiment 7

A method of embodiment 6, wherein the at least one enzyme is selected from the group consisting of pectinase, hemicellulase, cellulase, and beta-glucosidase, or combination thereof.

Embodiment 8

A method of embodiment 1, 2, 3, 4, 5, 6, or 7, wherein the citrus waste is derived from orange or grapefruit peel.

Embodiment 9

A method of embodiment 1, 2, 3, 4, 5, 6, 7, or 8, wherein the contacting in step (a) reduces the level of at least one compound in the citrus waste capable of inhibiting the fermentation in step (c).

Embodiment 10

A method of embodiment 1, 2, 3, 4, 5, 6, 7, 8, or 9, wherein the contacting of step (a) reduces the level of the at least one compound in the citrus waste capable of inhibiting the fermentation in step (c) to below about 3000 parts per million based on the weight of citrus waste in the mixture from step (a).

Embodiment 11

A method of embodiment 1, 2, 3, 4, 5, 6, 7, 8, 9, or 10, wherein the contacting of step (a) reduces the presence of the at least one compound capable of inhibiting the fermentation in step (c) to below about 1500 parts per million.

Embodiment 12

A method of embodiment 1, 2, 3, 4, 5, 6, 7, 8, 9 10, or 11, wherein the hydrolyzing and the fermenting are performed substantially simultaneously.

Embodiment 13

A method of embodiment 1, 2, 3, 4, 5, 6, 7, 8, 9, 10, 11, or 12, wherein the fermenting is performed by contacting the mixture from step (c) with an ethanol producing organism selected from a yeast, bacteria, or fungi.

Embodiment 14

A method of embodiment 13, wherein the organism is selected from brewer's yeast, *S. cerevisiae*, and *E. coli* strain KO11.

Embodiment 15

A method of embodiment 13 or 14, wherein the organism is *E. coli* strain KO11.

Embodiment 16

A method of embodiment 1, 2, 3, 4, 5, 6, 7, 8, 9, 10, 11, 12, 13, 14, or 15, wherein the ethanol is isolated by distillation.

Embodiment 17

A method for producing ethanol from citrus waste of embodiment 1, comprising:

a. hydrolyzing an aqueous citrus waste mixture to provide an aqueous citrus waste mixture comprising fermentable sugars derived from citrus waste (saccharification);
b. contacting the aqueous citrus waste mixture comprising fermentable sugars derived from citrus waste from step (a) with a suitable extraction solvent (or solvent mixture) to provide an aqueous citrus waste mixture with a reduced level of at least one compound capable of inhibiting a fermentation of sugars derived from citrus waste;
c. fermenting the aqueous citrus waste mixture with a reduced level of at least one compound capable of inhibiting a fermentation of sugars derived from citrus waste obtained from step (b) to produce a mixture containing ethanol; and
d. isolating the ethanol from the fermented mixture from step (c).

Embodiment 18

A method of embodiment 17, wherein the hydrolyzing and fermenting are performed substantially simultaneously.

Embodiment 19

A method of embodiment 17 or 18, wherein the citrus waste is derived from orange or grapefruit peel.

Embodiment 20

A method of embodiment 17, 18, or 19, wherein contacting in step (b) reduces the level of at least one compound capable of inhibiting the fermentation in step (c).

Embodiment 21

A method of embodiment 17, 18, 19 or 20, wherein substantially all of the at least one compound capable of inhibiting the fermentation in step (c) is reduced to a level below about 3000 parts per million based on the weight of citrus waste in the mixture from step (a).

Embodiment 22

A method of embodiment 1, 2, 3, 4, 5, 6, 7, 8, 9, 10, 11, 12, 13, 14, 15, 16, 17, 18, 19, 20, or 21, wherein the suitable extraction solvent is a supercritical fluid extraction solvent.

Embodiment 23

A method of embodiment 22, wherein the suitable extraction solvent is selected from the group consisting of supercritical: carbon dioxide, ethylene, propane, propylene, trifluoromethane, chlorotrifluoromethane, trichlorofluoromethane, cyclohexane, n-pentane, or toluene.

Embodiment 24

A method of embodiment 23, wherein the suitable extraction solvent is supercritical carbon dioxide.

Embodiment 25

A method of embodiment 1, 2, 3, 4, 5, 6, 7, 8, 9, 10, 11, 12, 13, 14, 15, 16, 17, 18, 19, 20, or 21, wherein the suitable extraction solvent is an ether, aryl, or hydrocarbon extraction solvent.

Embodiment 26

A method of embodiment 25, wherein the suitable extraction solvent is an ether solvent selected from the group consisting of: diethyl ether, diethoxymethane, ethylene glycol dimethyl ether, ethylene glycol diethyl ether, diethylene glycol dimethyl ether, diethylene glycol diethyl ether, triethylene glycol dimethyl ether and t-butyl methyl ether, or a mixture thereof.

Embodiment 27

A method of embodiment 25, wherein the suitable extraction solvent is an aryl solvent selected from the group consisting of: benzene, toluene, ethylbenzene, o-xylene, m-xylene or p-xylene, or a mixture thereof.

Embodiment 28

A method of embodiment 25, wherein the suitable extraction solvent is a hydrocarbon solvent selected from the group consisting of: pentane, hexane, heptane, octane, nonane, decane, dimethyloctane, trimethylpentane, cyclohexane, cycloheptane, decalin, methylcyclohexane, or any mixture thereof.

Embodiment 29

A method of embodiment 28, wherein the suitable extraction solvent is a hydrocarbon solvent selected from the group consisting of: heptane, octane, nonane, decane, dimethyloctane, trimethylpentane, cyclohexane, cycloheptane, decalin, methylcyclohexane, or any mixture thereof.

Embodiment 30

A method of embodiment 29, wherein the suitable extraction solvent is a hydrocarbon solvent selected from the group consisting of: octane, nonane, decane, dimethyloctane, trimethylpentane, cyclohexane, cycloheptane, decalin, methylcyclohexane, or any mixture thereof.

Embodiment 31

A method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the at least one compound capable of inhibiting a fermentation of sugars derived from citrus waste is limonene.

Embodiment 32

A method of embodiment for producing ethanol from citrus waste, comprising providing an aqueous mixture comprising citrus waste, extracting with a suitable solvent or solvent mixture at least a portion of one or more fermentation-inhibitory compounds contained in the citrus waste, converting one or more polysaccharides contained in the citrus waste into fermentable sugars, and fermenting the sugars to produce ethanol.

Embodiment 33

A method of embodiment 32, wherein the citrus waste is derived from orange or grapefruit peel.

Embodiment 34

A method of embodiment 32 or 33, comprising:
a. extracting the aqueous mixture comprising citrus waste to remove at least a portion of one or more fermentation-inhibitory compounds from the aqueous mixture;
b. converting at least a portion of the one or more polysaccharides contained in the aqueous mixture from step (a) into fermentable sugars; and
c. fermenting the aqueous mixture from step (b) to produce a fermented mixture containing ethanol.

Embodiment 35

A method of embodiment 32, 33, or 34, wherein the ethanol is isolated from the fermented mixture.

Embodiment 36

A method of embodiment 32, 33, 34, or 35, wherein the suitable extraction solvent is a supercritical fluid extraction solvent.

Embodiment 37

A method of embodiment 36, wherein the suitable supercritical extraction solvent is selected from the group consisting of: carbon dioxide, ethylene, propane, propylene, trifluoromethane, chlorotrifluoromethane, trichlorofluoromethane, cyclohexane, n-pentane, and toluene.

Embodiment 38

A method of embodiment 36 or 37, wherein the suitable extraction solvent is supercritical carbon dioxide.

Embodiment 39

A method of embodiment 32, 33, 34, or 35, wherein the suitable extraction solvent is selected from the group consisting of: an ether, an aryl, and a hydrocarbon extraction solvent, or any mixture thereof.

Embodiment 40

A method of embodiment 32, 33, 34, 35, or 39, wherein the converting comprises saccharifying the polysaccharides.

Embodiment 41

A method of embodiment 32, 33, 34, 35, or 39, wherein the converting further comprises adding water to the aqueous mixture comprising citrus waste prior to saccharifying the polysaccharides.

Embodiment 42

A method of embodiment 32, 33, 34, 35, or 39, wherein the suitable extraction solvent is an ether solvent selected from the group consisting of: diethyl ether, diethoxymethane, ethylene glycol dimethyl ether, ethylene glycol diethyl ether, diethylene glycol dimethyl ether, diethylene glycol diethyl ether, triethylene glycol dimethyl ether, and t-butyl methyl ether, or any mixture thereof.

Embodiment 43

A method of embodiment 32, 33, 34, 35, 36, 37, 38, 39, 40, 41, or 42, wherein the suitable extraction solvent is an aryl solvent selected from the group consisting of: benzene, toluene, ethylbenzene, o-xylene, m-xylene, and p-xylene, or any mixture thereof.

Embodiment 44

A method of embodiment 43, wherein the suitable extraction solvent is a hydrocarbon solvent selected from the group consisting of: pentane, hexane, heptane, octane, nonane, decane, dimethyloctane, trimethylpentane, cyclohexane, cycloheptane, decalin, and methylcyclohexane, or any mixture thereof.

Embodiment 45

A method of embodiment 32, 33, 34, 35, 36, 37, 38, 39, 40, 41, 42, 43, or 44, wherein the citrus waste is in a particle form provided by milling or grinding.

Embodiment 46

A method of embodiment 45, wherein the citrus waste is provided in the form of particles with an average particle size of less than about 0.5 inches.

Embodiment 47

A method of embodiment 45 or 46, wherein the average particle size of the citrus waste is less than about 0.1 inches.

Embodiment 48

A method of embodiment 32, 33, 34, 35, 36, 37, 38, 39, 40, 41, 42, 43, 44, 45, 46, or 47, wherein the one or more polysaccharides contained in the citrus waste are contacted with at least one enzyme capable of complex carbohydrate hydrolysis to substantially saccharify the polysaccharides.

Embodiment 49

A method of embodiment 48, wherein the at least one enzyme is selected from the group consisting of pectinase, hemicellulase, cellulase, and beta-glucosidase, or any combination thereof.

Embodiment 50

A method of embodiment 32, 33, 34, 35, 36, 37, 38, 39, 40, 41, 42, 43, 44, 45, 46, 47, 48, or 49, wherein the extracting reduces the presence of the one or more fermentation-inhibitory compounds in the citrus waste to a level below about 3000 parts per million based on the weight of citrus waste in the mixture from step (a).

Embodiment 51

A method of embodiment 50, wherein the extracting reduces the presence of the one or more fermentation-inhibitory compounds in the citrus waste to a level below about 1500 parts per million.

Embodiment 52

A method of embodiment 43, 44, 48, or 49, wherein the saccharifying and the fermenting are performed substantially simultaneously.

Embodiment 53

A method of embodiment 32, 33, 34, 35, 36, 37, 38, 39, 40, 41, 42, 43, 44, 45, 46, 47, 48, 49, 50, 51, or 52, wherein the fermenting is performed by contacting the mixture from step (b) with an ethanol producing organism selected from a yeast, bacteria, and fungi.

Embodiment 54

A method of embodiment 53, wherein the organism is selected from brewer's yeast, *S. cerevisiae*, and *E. coli* strain KO11.

Embodiment 55

A method of embodiment 53 or 54, wherein the organism is *E. coli* strain KO11.

Embodiment 56

A method of embodiment 35, 36, 37, 38, 39, 40, 41, 42, 43, 44, 45, 46, 47, 48, 49, 50, 51, 52, 53, 54, or 55, wherein the ethanol is isolated by distillation.

Embodiment 57

A method of embodiment 32 or 33, comprising:
a. converting into fermentable sugars one or more citrus waste polysaccharides contained in the aqueous mixture comprising citrus waste;
b. extracting the aqueous mixture from step (a) to remove at least a portion of one or more fermentation-inhibitory compounds; and
c. fermenting the extracted aqueous mixture from step (b) to produce a fermented mixture containing ethanol.

Embodiment 58

A method of embodiment 57, wherein the ethanol is isolated from the fermented mixture.

Embodiment 59

A method of embodiment 57 or 58, wherein the suitable extraction solvent is a supercritical fluid extraction solvent.

Embodiment 60

A method of embodiment 59, wherein the suitable supercritical extraction solvent is selected from the group consisting of: carbon dioxide, ethylene, propane, propylene, trifluoromethane, chlorotrifluoromethane, trichlorofluoromethane, cyclohexane, n-pentane, and toluene.

Embodiment 61

A method of embodiment 59 or 60, wherein the suitable supercritical extraction solvent is carbon dioxide.

Embodiment 62

A method of embodiment 57 or 58, wherein the suitable extraction solvent is selected from the group consisting of: an ether, an aryl, and a hydrocarbon extraction solvent, or any mixture thereof.

Embodiment 63

A method of embodiment 57, 58, or 62, wherein the suitable extraction solvent is an ether solvent selected from the group consisting of: diethyl ether, diethoxymethane, ethylene glycol dimethyl ether, ethylene glycol diethyl ether, diethylene glycol dimethyl ether, diethylene glycol diethyl ether, triethylene glycol dimethyl ether and t-butyl methyl ether, or any mixture thereof.

Embodiment 64

A method of embodiment 57, 58, or 62, wherein the suitable extraction solvent is an aryl solvent selected from the group consisting of: benzene, toluene, ethylbenzene, o-xylene, m-xylene, and p-xylene, or any mixture thereof.

Embodiment 65

A method of embodiment 57, 58, or 62, wherein the suitable extraction solvent is a hydrocarbon solvent selected from the group consisting of: pentane, hexane, heptane, octane, nonane, decane, dimethyloctane, trimethylpentane, cyclohexane, cycloheptane, decalin, menthane, and methylcyclohexane, or any mixture thereof.

Embodiment 66

A method of embodiment 57, 58, 59, 60, 61, 62, 63, 64, or 65, further comprising: removing water from the aqueous mixture comprising converted citrus waste from step (a) prior to extracting with the suitable extraction solvent; or adding water to the aqueous citrus waste mixture from step (b) prior to fermenting said aqueous citrus waste mixture; or both.

Embodiment 67

A method of embodiment 57, 58, 59, 60, 61, 62, 63, 64, 65, or 66, wherein the converting and fermenting are performed substantially simultaneously.

Embodiment 68

A method of embodiment 57, 58, 59, 60, 61, 62, 63, 64, 65, 66, or 67, wherein the extracting reduces the level of the one or more fermentation-inhibiting compounds to a level below about 3000 parts per million based on the weight of citrus waste in the aqueous mixture from step (a).

Embodiment 69

A method of embodiment 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68, wherein one of the one or more fermentation-inhibitory compounds is limonene.

Embodiment 70

A method for producing ethanol from citrus waste, comprising:
(a) extracting a mixture comprising citrus waste containing one or more fermentation-inhibitory compounds with an extraction solvent to provide an extracted citrus waste mixture having a reduced concentration of at least one of the fermentation-inhibitory compounds; and
(b) producing ethanol from the extracted mixture.

Embodiment 71

A method for producing ethanol from citrus waste, comprising:
(a) providing a mixture which comprises citrus waste, wherein the concentration of at least one fermentation-inhibitory compound in the citrus waste has been reduced by solvent extraction; and
(b) producing ethanol from the aqueous mixture.

Embodiment 72

A method for producing ethanol from citrus waste, comprising:
(a) providing a mixture which comprises citrus waste having a reduced concentration of at least one fermentation-inhibitory compound; and
(b) producing ethanol from the aqueous mixture.

Embodiment 73

A method of embodiment 70, 71, or 72, wherein the citrus waste is derived from orange or grapefruit peel.

Embodiment 74

A method of embodiment 70, wherein the extraction solvent is a supercritical fluid extraction solvent.

Embodiment 75

A method of embodiment 74, wherein the supercritical fluid extraction solvent is selected from the group consisting of carbon dioxide, ethylene, propane, propylene, trifluoromethane, chlorotrifluoromethane, trichlorofluoromethane, cyclohexane, n-pentane, and toluene, or any mixtures thereof.

Embodiment 76

A method of embodiment 75, wherein the supercritical fluid extraction solvent is carbon dioxide.

Embodiment 77

A method of embodiment 70, wherein the extraction solvent is selected from the group consisting of an ether solvent, an aromatic solvent, and a hydrocarbon solvent, or any mixtures thereof.

Embodiment 78

A method of embodiment 77, wherein the extraction solvent is an ether solvent selected from the group consisting of diethyl ether, diethoxymethane, ethylene glycol dimethyl ether, ethylene glycol diethyl ether, diethylene glycol dimethyl ether, diethylene glycol diethyl ether, triethylene glycol dimethyl ether, and t-butyl methyl ether, or any mixtures thereof.

Embodiment 79

A method of embodiment 1, 2, 3, 4, 5, 6, 7, 8, 9, 10, 11, 12, 13, 14, 15, 16, 17, 18, 19, 20, 21, 25, or 77, wherein the extraction solvent is an aromatic solvent selected from the group consisting of benzene, toluene, ethylbenzene, o-xylene, m-xylene, and p-xylene, mesitylene, and durene, or any mixtures thereof.

Embodiment 80

A method of embodiment 1, 2, 3, 4, 5, 6, 7, 8, 9, 10, 11, 12, 13, 14, 15, 16, 17, 18, 19, 20, 21, 25, or 77 wherein the extraction solvent is a hydrocarbon solvent selected from the group consisting of pentane, hexane, heptane, octane, nonane, decane, dimethyloctane, trimethylpentane, cyclohexane, cycloheptane, decalin, menthane, and methylcyclohexane, or any mixtures thereof.

Embodiment 81

A method of embodiment 80, wherein the extraction solvent is a hydrocarbon solvent selected from the group consisting of pentane, hexane, heptane, octane, nonane, decane, dimethyloctane, trimethylpentane, cyclohexane, cycloheptane, decalin, and methylcyclohexane, or any mixtures thereof.

Embodiment 82

A method of embodiment 1, 2, 3, 4, 5, 6, 7, 8, 9, 10, 11, 12, 13, 14, 15, 16, 17, 18, 19, 20, 21, 25, 77, or 80 wherein the extraction solvent comprises one or more isomers of menthane.

Embodiment 83

A method of embodiment 70, 71, 72, 73, 74, 75, 76, 77, 78, 79, 80, 81, or 82, further comprising providing the citrus waste in step (a) in the form of particles with an average particle size of less than about 0.5 inches.

Embodiment 84

A method of embodiment 83, wherein the average particle size of the citrus waste is less than about 0.1 inches.

Embodiment 85

A method of embodiment 70, 74, 75, 76, 77, 78, 79, 80, 81, 82, 83, or 84, wherein the particles are prepared by a method which comprises milling or grinding.

Embodiment 86

A method of embodiment 70, 74, 75, 76, 77, 78, 79, 80, 81, 82, 83, 84, or 85, wherein the extracting reduces the concentration of at least one of the fermentation-inhibitory compounds in the citrus waste to a level below about 3000 parts per million based on the weight of citrus waste in the mixture from step (a).

Embodiment 87

A method of embodiment 86, wherein the extracting reduces the concentration of at least one of the fermentation-inhibitory compounds in the citrus waste to a level below about 1500 parts per million.

Embodiment 88

A method of embodiment 70, 71, 72, 73, 74, 75, 76, 77, 78, 79, 80, 81, 82, 83, 84, 85, 86, or 87, wherein the ethanol is produced in step (b) by a process comprising fermenting the extracted mixture.

Embodiment 89

A method of embodiment 88, wherein the fermenting is performed by contacting the extracted mixture from step (b) with an ethanol producing organism selected from a yeast, bacteria, and fungi.

Embodiment 90

A method of embodiment 89, wherein the organism is selected from brewer's yeast, *S. cerevisiae*, and *E. coli* strain KO11.

Embodiment 91

A method of embodiment 90, wherein the organism is *E. coli* strain KO11.

Embodiment 92

A method of embodiment 88, 89, 90, or 91, further comprising isolating the ethanol from the fermented mixture.

Embodiment 93

A method of embodiment 92, wherein the ethanol is isolated by distillation.

Embodiment 94

A method of embodiment 88, 89, 90, 91, 92, or 93, wherein the fermentation process comprises:
(i) converting one or more polysaccharides contained in the citrus waste into fermentable sugars; and
(ii) fermenting the sugars to produce ethanol.

Embodiment 95

A method of embodiment 94, wherein step (i) comprises saccharifying the polysaccharides.

Embodiment 96

A method of embodiment 95, wherein step (i) further comprises adding water to the mixture prior to saccharification.

Embodiment 97

A method of embodiment 95 or 96, wherein the one or more polysaccharides contained in the citrus waste are contacted with at least one enzyme capable of complex carbohydrate hydrolysis to substantially saccharify the polysaccharides.

Embodiment 98

A method of embodiment 97, wherein the at least one enzyme is selected from the group consisting of pectinase, hemicellulase, cellulase, and beta-glucosidase, or combination thereof.

Embodiment 99

A method of embodiment 95, 96, 97, or 98, wherein the saccharifying and the fermenting are performed substantially simultaneously.

Embodiment 100

A method of claim 70, 73, 74, 75, 76, 77, 78, 79, 80, 81, 82, 83, 84, 85, 86, 87, 88, 89, 90, 91, 92, 93, 94, 95, 96, 97, 98, or 99, wherein one or more polysaccharides contained in the citrus waste are converted into fermentable sugars prior to the extracting in step (a).

Embodiment 101

A method of embodiment 100, wherein the converting comprises saccharifying the polysaccharides.

Embodiment 102

A method of embodiment 101, wherein the converting further comprises adding water to the mixture prior to saccharification.

Embodiment 103

A method of embodiment 102, wherein the one or more polysaccharides contained in the citrus waste are contacted with at least one enzyme capable of complex carbohydrate hydrolysis to substantially saccharify the polysaccharides.

Embodiment 104

A method of embodiment 103, wherein the at least one enzyme is selected from the group consisting of pectinase, hemicellulase, cellulase, and beta-glucosidase, or combination thereof.

Embodiment 105

A method of claim 102, 103, or 104, further comprising: removing at least a portion of the water from the converted citrus waste prior to the extracting.

Embodiment 106

A method of embodiment 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, or 105, wherein one of the one or more fermentation-inhibitory compounds is limonene.

What is claimed is:

1. A method for producing ethanol from citrus waste, comprising:
   a. contacting citrus waste with supercritical $CO_2$ to provide a citrus waste with a level below about 3000 parts per million of limonene;
   b. adding water to the citrus waste from step (a);
   c. hydrolyzing the aqueous mixture of citrus waste from step (b) by the addition of enzymes to provide an aqueous mixture comprising fermentable sugars derived from the citrus waste;
   d. fermenting the aqueous mixture obtained from step (c) to produce an aqueous mixture containing ethanol; and,
   e. removing the ethanol from the mixture from step (d).

2. A method of claim 1, further comprising providing the citrus waste to step (a) in the form of particles with an average particle size of less than about 0.5 inches.

3. A method of claim 2, wherein the average particle size of the citrus waste is less than about 0.1 inches.

4. A method of claim 2, wherein the providing comprises milling or grinding.

5. A method of claim 1, wherein the citrus waste is contacted with at least one enzyme capable of complex carbohydrate hydrolysis to substantially saccharify the polysaccharides contained in the citrus waste.

6. A method of claim 5, wherein the enzyme is selected from a pectinase, a hemicellulase, a cellulase, a beta-glucosidase, and combinations thereof.

7. A method of claim 1, wherein the citrus waste is derived from orange or grapefruit peel.

8. A method of claim 1, wherein the contacting of step (b) reduces the presence of the limonene to below about 1500 parts per million.

9. The method of claim 1, wherein the hydrolyzing and the fermenting are performed simultaneously.

10. The method of claim 1, wherein the fermenting is performed by contacting the mixture from step (c) with an ethanol producing organism selected from a yeast, bacteria, and fungi.

11. The method of claim 10, wherein the organism is *E. coli* strain KO11 or a yeast selected from brewer's yeast and *S. cerevisiae*.

12. The method of claim 11, wherein the organism is *E. coli* strain KO11.

13. The method of claim 1, wherein the ethanol is removed by distillation.

14. A method of claim 1, wherein contacting in step (c) reduces the level of at least one compound capable of inhibiting the fermentation in step (e).

15. A method for producing ethanol from citrus waste, comprising:
   a. hydrolyzing an aqueous mixture of citrus waste by the addition of enzymes to provide an aqueous mixture comprising fermentable sugars derived from the citrus waste;
   b. optionally removing water from the hydrolyzed citrus waste from step (a);
   c. contacting the citrus waste from step (a) or step (b) with supercritical $CO_2$ to provide a citrus waste with a level below about 3000 parts per million of limonene;
   d. optionally adding water to the citrus waste from step (c);
   e. fermenting the aqueous mixture obtained from step (c) or step (d) to produce an aqueous mixture containing ethanol; and,
   f. removing the ethanol from the mixture from step (e).

16. The method of claim 15, wherein the hydrolyzing and fermenting are performed simultaneously.

17. A method of claim 16, wherein the citrus waste is derived from orange or grapefruit peel.

* * * * *